United States Patent [19]
Nitecki et al.

[11] Patent Number: 5,089,261
[45] Date of Patent: Feb. 18, 1992

[54] PREPARATION OF A POLYMER/INTERLEUKIN-2 CONJUGATE

[75] Inventors: Danute E. Nitecki, Berkeley; Nandini Katre, El Cerrito; Robert J. Goodson, Albany; Lois Aldwin, San Mateo, all of Calif.

[73] Assignee: Cetus Corporation, Emeryville, Calif.

[21] Appl. No.: 415,046

[22] Filed: Sep. 29, 1989

Related U.S. Application Data

[63] Continuation of Ser. No. 299,235, Jan. 23, 1989, Pat. No. 4,902,502.

[51] Int. Cl.$^5$ .................. A61K 31/745; A61K 45/05; C07K 17/00
[52] U.S. Cl. .................. 424/85.2; 424/85.1; 530/402; 530/409; 530/351; 514/2
[58] Field of Search .................. 424/85.1, 78, 83, 85.2; 530/351, 402, 409; 514/2

[56] References Cited

U.S. PATENT DOCUMENTS

| | | | |
|---|---|---|---|
| 4,604,377 | 8/1986 | Fernandez et al. | 435/69.52 |
| 4,766,106 | 8/1988 | Katre et al. | 424/83 |
| 4,818,769 | 4/1989 | Nunberg et al. | 514/2 |

FOREIGN PATENT DOCUMENTS

| | | |
|---|---|---|
| 0154316 | 11/1985 | European Pat. Off. . |
| 62-185029 | 8/1987 | Japan . |
| 62-252800 | 11/1987 | Japan . |
| 63-258896 | 10/1988 | Japan . |
| 2189393 | 10/1987 | United Kingdom . |

OTHER PUBLICATIONS

Veronese, "Surface modification of proteins," Applied Biochem and Biotechnology, vol. 11, 1985, p. 141.
Dayhoff, M., Atlas of Protein Sequence & Structure, vol. 5:89-99, 1972.

*Primary Examiner*—Howard E. Schain
*Assistant Examiner*—Susan M. Perkins
*Attorney, Agent, or Firm*—Philip L. McGarrigle

[57] ABSTRACT

The present invention is a process for preparing a pharmaceutical composition comprising a biologically active conjugated protein. It comprises a polyethylene glycol or a polyoxyethylated polyol conjugated to IL-2. This protein is conjugated to reduce its immunogenicity, and increase its solubility, and increase its circulating in vivo half-life.

11 Claims, No Drawings

PREPARATION OF A POLYMER/INTERLEUKIN-2 CONJUGATE

This application is a continuation of application Ser. No. 07/299,235, filed Jan. 23, 1989, now U.S. Pat. No. 4,902,502.

FIELD OF THE INVENTION

The present invention is a process for chemically modifying a protein to alter the protein's physical or chemical properties. More specifically, the present invention describes a method for preparing an active polymer ester, and the conjugate that is formed when it is attached to Interleukin-2 (IL-2).

BACKGROUND OF THE INVENTION

Various natural and recombinant proteins have medical and pharmaceutical utility. Once they have been purified, separated, and formulated, they can be parenterally administered to disadvantaged hosts. However, parenterally administered proteins may stimulate an immune response, may be relatively water insoluble, and may have suboptimal pharmokinetic behavior. Consequently, it can be difficult to achieve therapeutically useful blood levels in patients.

These problems may be overcome by conjugating the proteins to polymers. For example, polyethylene glycol (PEG) can be conjugated to proteins for various purposes. Davis et al., U.S. Pat. No. 4,179,337 discloses conjugating polyethylene glycol to polypeptides, such as enzymes and insulin. Davis et al. made these conjugates so that the protein would be less immunogenic and would retain a substantial proportion of its physiological activity. Davis et al. also disclose methods for placing a reactive group on PEG and subsequently conjugating it to a protein. Iwashita et al., U.S. Pat. No. 4,412,989, disclose covalently conjugating polyethylene glycol to an oxygen carrying molecule. This conjugate is useful as a blood substitute. Veronese et al., *Applied Biochem. and Biotech.*, 11:141–152 (1985) disclose activating polyethylene glycols with phenyl chloroformates to modify a ribonuclease and a superoxide dismutase. Katre et al., U.S. Pat. No. 4,766,106 also disclose solubilizing proteins by polymer conjugation. For example, PEG, and other polymers, are conjugated to recombinant proteins to reduce immunogenicity and increase in vivo blood levels, among other things. These compounds may more specifically include interleukin-2 (IL-2), interferon-$\beta$ (IFN-$\beta$), immunotoxins, and other proteins that share similar characteristics. Nishimura et al., European Patent Application 154,316 and Tomasi International Application Number PCT/US85/02572, disclose similar subject matter.

The process for attaching PEG to these useful recombinant proteins is important. Some processes may be better than others due to their simplicity, their specificity, and the stability they give to the protein/PEG conjugate. Accordingly, the present invention is a process, and a conjugate, to provide those advantages.

SUMMARY OF THE INVENTION

The present invention is a method for producing a polyethylene glycol (PEG) IL-2 conjugate or a polyoxyethylated polyol (POP) IL-2 conjugate comprising contacting PEG or POP, which has at least one hydroxyl group, and a chloroformate under the appropriate reaction conditions to form a PEG or POP active ester; and contacting the PEG or POP active ester with IL-2 under the appropriate reaction conditions. Preferably, the ratio of PEG or POP active ester to IL-2 is between 1 and 20, more preferable between 6 and 16. Preferably, the final PEG or POP/IL-2 conjugate has a ratio of between 1 and 3 PEGs or POPs per IL-2, more preferably between 2 and 3. Preferably, the PEG or POP has a molecular weight between 1000 and 40,000, more preferably between 2000 and 20,000, most preferably between 3,000 and 12,000.

Among other factors, it has been discovered that the present invention produces a relatively more stable PEG/IL-2 conjugate, which is relatively easy to purify. It has also been discovered that PEG can be more selectively attached to IL-2 which can produce these more desirable PEG/IL-2 conjugates.

More specifically, the present invention comprises a method for producing a PEG/IL-2 conjugate, comprising contacting PEG, having a terminal hydroxy group, with para-nitrophenyl chloroformate under the appropriate reaction conditions to form a PEG activate ester; and contacting the PEG active ester with des-ala ser$_{125}$, IL-2 to form a PEG/IL-2 conjugate.

DETAILED DESCRIPTION OF THE INVENTION

As mentioned above, the present invention is a process designed to produce a novel PEG/IL-2 and POP/IL-2 conjugate. This process can stably solubilize, reduce the immunogenicity, and increase the circulating half-life of IL-2. These are advantages when IL-2 is administered to humans or animals. Furthermore, this specific PEG/IL-2 conjugate or POP/IL-2 conjugate can be relatively more stable and easier to purify than conjugates prepared by other methods. Without wishing to be bound by theory, we believe that the present process is advantageous because the attachment of PEG to IL-2 can be relatively predictable and selective.

In the present invention, purified IL-2 is convalently conjugated to a homopolymer of polyethylene glycol (PEG) or a polyoxyethylated polyol (POP). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the IL-2. However, it will be understood that the type and amount of the reactive groups may be varied to achieve a covalently conjugated PEG/IL-2 of the present invention.

Water soluble polyoxyethylated polyols are all useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al. *J. Bio. Chem.*, 263:15064–15070(1988) and a discussion of POG/IL-2 conjugates is found in U.S. Pat. No. 4,766,106, both of which are hereby incorporated by reference in their entireties.

The following discussion is directed to the conjugation of these water soluble polymers to IL-2. It should be understood that even though PEG or POG is mentioned, the other recited water soluble polymers can be used.

The PEG or POG is attached to IL-2 by covalent conjugation. "Covalently conjugated" or "conjugated" refer to the attachment of PEG or POG to IL-2 via an activated PEG or POG. "Active" or "activated" describes the attachment of a reactive group onto a PEG or POG hydroxyl (—OH) group, so that they can be conjugated to IL-2. Generally, the PEG or POG molecule is activated by attaching the reactive group to a hydroxyl group and then the active molecule is covalently conjugated to an amino group or IL-2. While conjugation may occur between any reactive amino acids on the protein, the reactive amino acid is preferably lysine. The lysine is linked to a reactive group on PEG or POG through its free $\epsilon$-amino group.

As stated above, PEG or POG is attached to IL-2. Interleukin-2 (IL-2) is a lymphokine which is produced by normal peripheral blood lymphocytes and is present in the body at low concentrations. It induces the proliferation of antigen or mitogen stimulated T cells after exposure to plant lectins, antigens, or other stimuli. IL-2 was first described by Morgan, D.A., et al., *Science* (1976) 193:1007–1008 and originally called T cell growth factor because of its ability to induce proliferation of stimulated T lymphocytes. It is a glyco-protein with a reported native molecular weight in the approximate range of 13,000 to 17,000 daltons (S. Gillis and J. Watson, *J. Exp. Med.*, 1980, 159:1709) and has an isoelectric point in the approximate pH range of 6–8.5. It is now recognized that in addition to its growth factor properties, it modulates various in vitro and in vivo functions of the immune system. IL-2 is one of several lymphocyte-produced messenger/regulatory molecules that mediate cellular interactions and functions.

IL-2 was initially made by cultivating human peripheral blood lymphocytes (PBLs) or other IL-2 producing cell lines; see, for example, U.S. Pat. No. 4,401,756, and Mertelsmann, et al. European Patent Publication No. 92,163 and U.S. Ser. No. 603,580, filed Apr. 25, 1984. However, recombinant DNA technology has provided an alternative to PBLs and cell lines for producing IL-2. For example, Taniguchi, T., et al., *Nature*, 1983, 302:305–310, Taniguchi et al., U.S. Pat. No. 4,738,927, and Devos, R., *Nucleic Acids Research*, 1983, 11:4307–4323, have reported cloning the human IL-2 gene and expressing it in microorganisms.

Modifications to the primary structure itself, by deletion, addition, or alteration of the amino acids incorporated into the sequence during translation, can be made without destroying the activity of the protein. Such modified proteins, known as "muteins", are described in U.S. Pat. No. 4,518,584 issued May 21, 1985, and U.S. Pat. No. 4,752,585, issued June 21, 1985, both are hereby incorporated by reference in their entireties. For example, at least one cysteine residue which is: not essential to biological activity; is present in the biologically active protein; and is free to form a disulfide link, may be replaced with a conservative amino acid to eliminate sites for undesirable intermolecular crosslinking or incorrect intramolecular disulfide bond formation. The crosslinking is undesirable if it changes the IL-2 conformation to render it essentially inactive for the present purpose. Also, it may be preferable to replace a methionine which is not essential to bioactivity. A conservative amino acid alteration in these contexts is defined as one which does not significantly adversely affect biological activity and involves substitutions of the amino acid. The conservative amino acids that may be substituted for cysteine and methionine are shown in the patents discussed above. Preferably they include at least: serine, alanine, glycine, valine, threonine, leucine, isoleucine, and tyrosine. More preferably they include serine and alanine. Most preferably, cysteine is replaced with serine and methionine is replaced with alanine. A preferred IL-2 mutein is one that has the cysteine at position 125 replaced with a conservative amino acid, such as serine. This mutein is more fully described in U.S. Pat. No. 4,518,584. Another preferred IL-2 mutein replaces the methionine at amino acid position 4 with a conservative amino acid, such as an alanine residue. This mutein is more fully described in U.S. Pat. No. 4,752,585. Other preferred IL-2 muteins include those which have as many as six amino acid deletions from the N-terminus. For example, des-ala$_1$ des-pro$_2$ des-thr$_3$ des-ser$_4$ des-ser$_5$ des-ser$_6$ IL-2 is an N-minus six mutein, other muteins may have fewer amino acid deletions. Specifically preferred muteins are des-ala$_1$ des-pro$_2$ des-thr$_3$ des-ser$_4$ ala$_{104}$ ser$_{125}$ IL-2, to name a few. Additionally, the IL-2 of the present invention can have amino acid deletions from the C-terminus. For example, one to six deletions may be made from the C-terminus.

IL-2 can be produced by a prokaryotic microorganism or a eukaryotic cell that has been transformed with a native or modified human IL-2 DNA sequence. It is unglycosylated when produced in *E. coli*. The IL-2 DNA useful in the present invention encodes a protein having: (a) an amino acid sequence that is substantially identical to the amino acid sequence of native human IL-2; (b) includes the disulfide bond between cysteines at positions 58 and 105, and (c) has a bioactivity that is similar to native human IL-2. Substantial identity of amino acid sequences means the sequences are identical or differ by one or more amino acid alterations (deletions, additions, substitutions) that do not cause a substantially adverse functional dissimilarity between the mutationally altered protein and native human IL-2. For examples of such proteins see: European Patent Application No. 83101035.0 filed Feb. 3, 1983 (published Oct. 19, 1983) under Publication No. 91539); European Patent Application No. 82307036.2 filed Dec. 22, 1982 (published Sept. 14, 1983 under Publication No. 88195); the recombinant IL-2 muteins described in European Patent Application No. 83306221.9 filed Oct. 13, 1983 (published May 30, 1984 under Publication No. 109748) which is the equivalent to Belgian Patent No. 893,016, commonly owned U.S. Pat. Nos. 4,518,584, and 4,752,585, and the recombinant IL-2 described in this application.

The precise chemical structure of IL-2 depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivitization using sugar moieties (glycosylation) or by other supplementary molecules such as lipids, phosphates, acetyl groups and the like. It may also be augmented by conjugation with saccharides or polymeric molecules. Certain aspects of such augmentation are accomplished through post-translational processing systems of the producing host, while other such modifications may be introduced in vitro. In any event, such modifications are acceptable so long as the affinity of the IL-2 molecule for its receptor is not significantly adversely affected. Further, individual amino acid residues in the chain may be modified by oxidation, reduction, or other derivitization, and the protein may be cleaved to obtain fragments which are still active in the present invention. Such alterations do not remove the protein sequence from the present definition of IL-2.

As mentioned previously, recombinant IL-2 can be produced by prokaryotic microorganisms or eukaryotic cells. Preferably, the IL-2 is produced by transforming a prokaryotic microorganism with DNA to produce a protein that possesses native human IL-2 activity. Examples of transformed microorganisms are described in European patent applications noted above. Bacteria are preferred prokaryotic microorganisms for producing IL-2 and $E.\ coli$ is especially preferred. A typical transformed microorganism useful in the present invention is $E.\ coli$ K-12, strain MM294, transformed with plasmid pLW1 (deposited at the American Type Culture Collection on Aug. 4, 1983 by Cetus Corporation under the provisions of the Budapest Treaty and having accession No. 39,405). Synthetic recombinant IL-2 can also be made in eukaryotes, such as yeast or human cells.

Processes for growing, harvesting, disrupting, or extracting the IL-2 from cells are substantially described in U.S. Pat. Nos. 4,604,377; 4,738,927; 4,656,132; 4,569,790; 4,748,234; 4,530,787; 4,572,298; U.S. Ser. Nos. 167,144; 48,408 and (Cetus case 2197.2, filed May 31, 1988), which are hereby incorporated by reference in their entireties. Other procedures for purifying native IL-2 from T cells are described by Watson, J. et al., *J. Exp. Med.*, 1979, 150:849–861; Gillis, S., et al., *J. Immunology*, 1980, 124:1954–1962; Mochizuki, D.Y., et al., *J. Immun Meth.*, 1980, 39:185–201; Welte, K., et al., *J. Exp. Med.*, 1982, 156:454–464; and European Patent Applications 83103582.9 (published Oct. 26, 1983 under No. 92163 and 83400938.3 published Nov. 16, 1983 under No. 94317) which are also incorporated by reference in their entireties.

The present invention reacts PEG-OH with a chloroformate (also called an alkyl chlorocarbonate) to form a PEG active ester. After the PEG active ester is formed, it is reacted with IL-2 to form a PEG/IL-2 conjugate. See also Veronese, et al., 1985, *Biochem. and Biotech.*, 11:141–152 which is hereby incorporated by reference in its entirety.

Chloroformates may be purchased from such companies as Aldrich, etc. They may also be made as shown in equation (1).

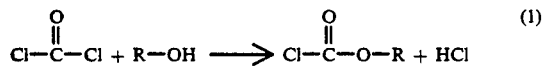
(1)

The chloroformate is made by reacting phosgene, also known as carbonyl chloride, with an alcohol (R—OH) which contains electron withdrawing substituents on the carbon that carries the —OH. The alcohol is preferably an acidic alcohol, more preferably an acidic alcohol which contains aromatic rings which have high extinction coefficients. Examples of R groups are: N-hydroxy-succinimide, N-hydroxy-sulfosuccinimides, cyanomethyl esters, all nitro, chloro, and cyano substitutions on benzene, naphthalene, or larger aromatic ring systems which may or may not contain hetero-atoms, such as pyridine, para-nitrophenol (PNP), ortho-nitrophenol (ONP), etc. Most preferred R groups are PNP and ONP.

After the chloroformate is formed, it is reacted with PEG-OH to form a PEG active ester as shown in equation (2).

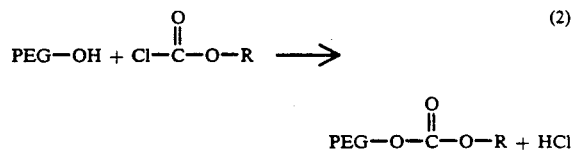

The chloroformate is reactive at two sites; at the bond between the chlorine and carbonyl group (more reactive) and the bond between the carbonyl and O—R group (less reactive). The more reactive site is where the chloroformate binds to the PEG.

PEG—OH and the chloroformate are preferably added together at room temperature in an appropriate solvent, such as $CHCl_3$, or $CH_2Cl_2$. Preferably an acylation catalyst is added between 0 and 1 hours later, preferably the catalyst is pyridine or dimethyl pyridine. Preferably, the chloroformate is added up to 12M excess, more preferably to a 2M excess. The mixture is allowed to mix for preferably at least 4 hours, more preferably at least 16 hours. At this point, a precipitate may form. It is removed by filtration and discarded. Filtering devices such as Whatman glass fiber filters (GH/B) are acceptable. The resulting solution contains the PEG active ester as well as unreacted PEG and excess chloroformate. It is precipitated by adding an ether, preferably the ether is diethyl ether. The precipitate contains the PEG active ester and can be washed with appropriate solvents such as ether, redissolved and reprecipitated if necessary.

After the PEG active ester is formed, it is conjugated with IL-2 as shown in equation (3):

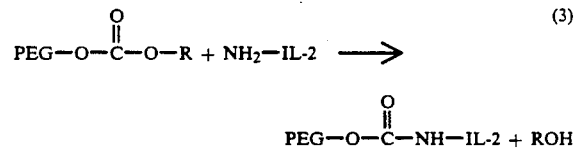

The chloroformate portion of the PEG active ester still has the less reactive site available. At this site, the covalent bond between the PEG and IL-2 is formed here. In the final product, the PEG moiety is bound to IL-2 by a urethane, also called a carbamate, bond. This bond is relatively stable and will keep PEG conjugated to IL-2 with little or no hydrolysis under physiological conditions.

The PEG active ester can be conjugated to IL-2 in the following manner. The PEG active ester is preferably diluted in an aqueous solution, such as 10 mM sodium acetate, pH 5.5. The IL-2 concentration is preferably between 0.5 and 10 mg/ml IL-2, more preferably between 1 and 5 mg/ml. The solution has a preferred pH range between 8 and 10, more preferably between 8.5 and 9.5 and a buffer which preferably comprises sodium borate or EPPS (N-(2-hydroxyethyl) piperazine-N-3-propane sulfonic acid, available from Sigma). The PEG active ester solution is added (at room temperature) to the IL-2 to a molar ratio preferably between 1 and 20 PEG active esters per IL-2, more preferably between 6 and 16 moles of PEG active esters per mole IL-2, and most preferably between 10 and 14 moles of PEG active esters per mole IL-2. Preferably the IL-2 and PEG active ester is allowed to react for between 10 minutes and 3 hours, more preferably between 30 minutes and 60 minutes. A final yield of between 1 and 3 PEGs per IL-2 is preferred. More preferably, the final conjugate contains between 2 and 3 PEGs per IL-2.

The conjugates which are produced by prior art methods can have a wide range of PEGs per IL-2. However, conjugates having the specific number of PEGs per IL-2 discussed above are preferred because they can be more effective for their intended purpose. If desired, these preferred PEG/IL-2 conjugates can be purified from the reaction mixture. There are many purification methods that are known to those of ordinary skill in the art such as size exclusion chromatography, hydrophobic interaction chromatography, ion exchange chromatography, preparative isoelectric focusing, etc. One particularly preferred method is to combine a size separation method with charge separation method, for example, size exclusion chromatography followed by ion exchange, see U.S. Ser. No. 253,708, which is hereby incorporated by reference in its entirety. Preferably, the size separation method is size exclusion chromatography which discriminates between molecules based on their hydrodynamic radius. Hydrodynamic radius is defined as the effective molecular radius of a particle in an aqueous environment. Preferably, the charge separation method is ion exchange chromatography which discriminates between molecules based on differential affinity of charged ions or molecules in solution for inert immobile charged substances. The size exclusion chromatography method and the ion exchange chromatography method comprise contacting a mixed solution of PEG/IL-2 conjugates with either column in the appropriate buffers and under the appropriate conditions. More preferably, the size exclusion chromatography column has the appropriate sieving capacity to size PEG/IL-2 conjugates with a molecular weight range preferably between 5,000 and 1,000,000. Example commercial columns are Sephacryl S-200, S-300, and S-400 HR (high resolution). More preferably, the ion exchange chromatography column can discriminate between individual species of PEG/IL-2 conjugates ranging in isoelectric point between 4 and 9, most preferably it can discriminate between PEG/IL-2 conjugates which range between 5.5 and 7.5 in isoelectric charge.

Typically, the output from either method, i.e. size exclusion chromatography or ion exchange chromatography, is a UV ($A_{280}$) absorbance profile of the eluted fractions some of which contain the conjugate. To determine which fractions contain the preferred conjugates (among other conjugates), the fractions can be screened against various standards. Preferred screening methods include SDS-PAGE, isoelectric focusing, bioactivity, and pharmacokinetics. Once it is known which fraction contains the preferred conjugates, those fractions may be further purified. For example, the polymer/protein conjugate mixture can be contacted with the size exclusion chromatography column, the fractions collected, then run on an SDS-PAGE gel to determine which fractions contain the preferred polymer/protein conjugates (among others). Then, the fractions of interest may be contacted with the ion exchange column, the fractions collected, and analyzed by isoelectric focusing to determine which fractions have the preferred polymer/protein conjugates. Before the PEG/IL-2 conjugate mixture is subjected to chromatography, it may be initially prepared by removing impurities. For example, salts may be removed with preparatory columns, or may be dialyzed against appropriate buffers.

Once the PEG/IL-2 is purified it may be tested for bioactivity using methods known in the art. For example, a HT-2 cell proliferation assay using the MTT stain is acceptable and is similar to the assay described by Gillis, et al., 1978, *J. Immunol.*, 120:2027–2032.

After the PEG/IL-2 is produced and purified it may be incorporated into a pharmaceutical composition because it is considered therapeutically effective for human and veterinary uses, such as cancer therapy and the treatment of infectious diseases. The PEG/IL-2 can be formulated in a nontoxic, inert, pharmaceutically acceptable aqueous carrier medium, preferably at a pH ranging from 3 to 8, more preferably ranging from 6 to 8. When used for in vivo therapy, the sterile PEG/IL-2 composition will comprise protein dissolved in an aqueous buffer having an acceptable pH upon reconstitution. The PEG/IL-2 can be formulated with a number of excipients such as amino acids, polymers, polyols, sugar, buffers, preservatives, other proteins, etc. Specific examples include: octylphenoxy polyethoxy ethanol compounds; polyethylene glycol monostearate compounds; polyoxyethylene sorbitan fatty acid esters; sucrose; fructose; dextrose; maltose; glucose; dextran; mannitol; sorbitol; inositol; galactitol; xylitol; lactose; trehalose; bovine or human serum albumin; citrate; acetate; Ringer's and Hank's solutions; saline; phosphate; cysteine; arginine; carnitine; alanine; glycine; lysine; valine; leucine; polyvinylpyrrolidone; polyethylene glycol; etc. Preferably this formulation is stable for at least 6 months at 4° C.

As a composition, it is parenterally administered to the subject by methods known in the art. This composition may contain other compounds that increase the effectiveness or promote the desirable qualities of IL-2. The composition must be safe for administration via the route that is chosen, sterile and effective. To maintain the sterility and to increase the stability of IL-2, the composition is lyophilized reconstituted prior to use.

Preferably, the formulation is suitable for parenteral administration to humans or animals in therapeutically effective amounts. These amounts may be determined by the in vivo efficacy data obtained after preclinical testing for: T-cell mutagenesis, cytotoxic T-cell induction, natural killer cell augmentation, IFN-$\beta$ induction, enhancement or restoration of cellular immunity (e.g. treatment of immune deficient conditions), and cell mediated anti-tumor activity.

IL-2 may also be administered in adoptive immunotherapy together with lymphokine activated lymphocytes, where the lymphocytes are reactive to a specific tumor. An example of this method is described in U.S. patent application Ser. No. 763,657 entitled "IL-2/Adoptive Immunotherapy" filed Aug. 8, 1985 by S. Rosenberg, et al., see also *New England Journal of Medicine*, 1985, 313:1485–1492.

The present process will now be illustrated by reference to the following examples which set forth particularly advantageous embodiments. However, it should be noted that these embodiments are illustrative and are not to be construed as restricting the invention in any way.

EXAMPLE I

PEG Active Ester Preparation

PEG was reacted with para-nitrophenyl chloroformate (PNP chloroformate) to produce the PEG active ester. The PNP chloroformate was obtained from Aldrich.

(A) 1.9 grams of PEG, having an average molecular weight of 1900 (purchased from Aldrich), was dissolved in approximately 13 ml of $CHCl_3$, and 1 gram of PNP chloroformate was added. The resulting solution was clear. After approximately 2 to 3 hours at room temperature, 1.5 ml of pyridine was added and a precipitate formed. The precipitate was removed by filtration using a Whatman glass microfiber filter (GF/B) and discarded. Approximately 200 ml of diethyl ether was added to the $CHCl_3$ solution. A large gelatinous precipitate formed which was filtered after 1 hour and washed with ether. The precipitate was dried to remove the ether. It contained the PEG active ester.

(B) 2.5 grams of PEG, having an average molecular weight of 5,000 (purchased from Aldrich), were dissolved in approximately 13 ml of $CHCl_3$. One gram of PNP chloroformate was added and the procedure noted above was repeated.

(C) Fifteen grams of PEG, having an average molecular weight of 6,000 (purchased from Union Carbide), were dissolved in approximately 75 ml of $CHCl_3$ and 20 ml of dry pyridine were added. The solution was cooled in ice and 6 grams of PNP chloroformate were added. $CHCl_3$ was added to bring the total volume to 100 ml; this was approximately a 12 fold molar excess over the PEG hydroxyl groups. After no more than 20 minutes, the solution was removed from the ice and stirred at room temperature for approximately 4 hours. A white precipitate was removed by filtration with the GF/B filter and washed with $CHCl_3$ (to bring the total volume to approximately 140 ml). The clear solution containing the PEG active ester was stirred vigorously and approximately 600 ml of dry ether were added. The resulting mixture was left for 48 hours to form a precipitate. This precipitate was collected on a glass frit filter, washed with dry ether, and dried in a vacuum.

(D) 7.5 grams of monomethyl PEG, having an average molecular weight of 6,000 (Union Carbide), were dissolved in approximately 45 ml of $CHCl_3$ and 3 grams of PNP chloroformate were added. After 1 hour, 9 ml dry pyridine were added and a precipitate formed. After cooling for a few minutes, the precipitate and solution were left to stand at room temperature for approximately 4 hours. The precipitate was removed by filtration with the GF/B filter, washed with $CHCl_3$ to produce a volume of approximately 70 ml, and ether was added to the solution to bring the total volume to approximately 400 ml. A precipitate was formed immediately and left to stand overnight. This precipitate was filtered, washed with dry ether, and vacuum dried. This procedure was also carried out with nitrophenyl chloroformate.

EXAMPLE II

Alternate PEG Active Ester Preparation 6 grams of monomethyl PEG was dissolved in 20 ml $CHCl_3$ in a 100 ml round-bottom flask. 2.4 grams of PNP chloroformate and 1.4 micrograms of DMAP (4-dimethylaminopyridine) were added to the round-bottom flask. The solution was stirred at room temperature under nitrogen for 3 hours. A white precipitate was formed by adding 400 ml ether to the above solution. This precipitate was separated by filtration using a frit-funnel and dried under vacuum. The precipitate was redissolved in 100 ml methylene chloride and the solution was filtered through filter paper. The filtrate was concentrated to a small volume and re-precipitated in 400 ml ether. A second precipitate was filtered and dried under vacuum.

EXAMPLE III

PEG/IL-2 Conjugation

The PEG active ester was produced in a manner similar to Example II, and the IL-2 was produced in a manner similar to that described in PCT Patent Publication WO 88/08849, published Nov. 17, 1988. Briefly, *E. coli* was transformed with a plasmid containing the IL-2 gene and the appropriate regulatory sequences. The *E. coli* was induced, the IL-2 was produced, and then recovered by the appropriate separation and purification methods.

An IL-2 solution was made, which contained 100 mM borate buffer and 2 mg/ml IL-2 at pH 9. Activated PEG esters were added to the IL-2 solution in a molar ratio of approximately 12:1 PEG active esters per IL-2. The solution was stirred at room temperature for 1 hour. The molar ratio of 12 PEGs per IL-2 was designed to produce a conjugate having a molar ratio of 2 or 3 PEGs per IL-2. As shown by SDS-PAGE, approximately 60% of the conjugates had a molar ratio of 2 or 3 PEGs per IL-2.

EXAMPLE IV

Conjugate Purification

The conjugates were concentrated using an Amicon stirred cell fitted with a YM 10 membrane. The conjugate concentrate was washed with 50 mM sodium acetate buffer at pH 5.5 to produce a final protein concentration of 35 mg/ml. The conjugate concentrate was loaded on a Sephacryl ® S-200 HR column equilibrated with a 50 mM sodium acetate buffer pH 5.5, and fractions were collected. Selected fractions, based on a UV absorbance profile, were run on reducing 12.5% SDS-PAGE and appropriate pools were made to select conjugates having a molar ratio of 2 or 3 PEGs per IL-2. Size exclusion HPLC (a Zorbax GF 250 column and a buffer containing 30 mM sodium phosphate at pH 7 and 100 mM sodium sulfate) was used to confirm that the pools contained predominantly a molar ratio of 2 and 3 PEGs per IL-2.

EXAMPLE V

Conjugate Formulation

The pools from Example IV were formulated at 1 mg/ml protein in either 20 mM citrate or 10 mM phosphate with 1% mannitol as a bulking agent with or without 1 mM EDTA. The formulated material was lyophilized.

The lyophilized cycle used was:
4 hour freeze at −50° C.
vacuum to 20–30 microns
ramp to −30° C. and hold for 42 hours
ramp to +15° C. 169 12° per hour and hold for at least 8 hours
nitrogen purge to −7.4 PSI approximately 15 inches Hg
stopper and bleed to atmospheric pressure For each formulation, the lyophilized vials were placed at −20° C., +4° C., 37° C., and 55° C. A set of formulations was also reconstituted with 1 ml of sterile water and kept at 37° C. The liquid samples were evaluated every week for 3 weeks. The lyophilized samples were monitored at 2 weeks and 5 weeks.

The lyophilized PEG/IL-2 conjugate of the present invention was stable when analyzed by SDS-PAGE and size exclusion chromatography (GF250 HPLC). For example, reconstituted samples, held for 3 weeks at 37° C., showed no evidence of hydrolysis of the conjugate.

The present invention has been described with reference to specific embodiments. However, this application is intended to cover those changes and substitutions which may be made by those skilled in the art without departing from the spirit and the scope of the appended claims.

We claim:

1. A pharmaceutically and therapeutically useful protein comprising a PEG or a polyoxyethylated polyol IL-2 conjugate made by contacting a PEG or a polyoxyethylated polyol, which has at least one hydroxyl group, with a chloroformate under the appropriate reaction conditions to form a PEG or a polyoxyethylated polyol active ester; and contacting the PEG or the polyoxyethylated polyol active ester with IL-2 under the appropriate reaction conditions to form a PEG/IL-2 conjugate or a polyoxyethylated polyol/IL-2 conjugate.

2. A PEG or a polyoxyethylated polyol IL-2 conjugate comprising PEG or a polyoxyethylated polyol covalently conjugated to IL-2 through a urethane bond.

3. A PEG or a polyoxyethylated polyol IL-2 conjugate having the structure:

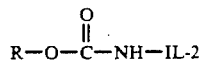

wherein R is the PEG or the polyoxyethylated polyol.

4. A conjugate in accordance with claim 2, wherein the conjugate has a molar ratio of from 1 and 3 PEGs per one IL-2.

5. A conjugate in accordance with claim 2, wherein the conjugate has a molar ratio of from 2 and 3 PEGs per one IL-2.

6. A conjugate in accordance with claim 2, wherein the IL-2 is a mutein.

7. A conjugate in accordance with claim 6, wherein the IL-2 mutein has up to six N-terminal deletions, and the cystein at position 125 is replaced by serine.

8. A therapeutically useful formulation comprising a PEG/IL-2 conjugate, wherein the PEG is covalently attached to IL-2 via a urethane bond, and at least one pharmaceutically acceptable excipient.

9. A PEG/IL-2 conjugate having the structure:

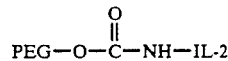

10. A therapeutically useful formulation in accordance with claim 8, wherein the at least one excipient comprises amino acids, polymers, polyols, sugars, buffers, preservatives, or other proteins.

11. A therapeutically useful formulation in accordance with claim 10, wherein the excipients are selected from the group consisting essentially of octylphenoxy polyethoxy ethanol compounds, polyethylene glycol monostereate compounds, polyoxyethylene sorbitan fatty acid esters, sucrose, fructose, dextrose, maltose, glucose, dextran, mannitol, sorbitol, inositol, galactitol, xylitol, lactose, trehalose, bovine or human serum albumin, citrate, acetate, Ringer's and Hank's solutions, saline, phosphate, cysteine, arginine, carnitine, alanine, glycine, lysine, valine, leucine, polyvinylpyrrilolidone, or polyethylene glycol.

* * * * *